United States Patent [19]

McGary, Jr. et al.

[11] Patent Number: 4,463,156
[45] Date of Patent: Jul. 31, 1984

[54] POLYURETHANE ELASTOMER AND AN IMPROVED HYPOALLERGENIC POLYURETHANE FLEXIBLE GLOVE PREPARED THEREFROM

[75] Inventors: Charles W. McGary, Jr., Centerville; Vincent J. Pascarella, Dayton; Delmer R. Rhodes; Robert A. Taller, both of Centerville, all of Ohio

[73] Assignee: Warner-Lambert Co., Inc., Morris Plains, N.J.

[21] Appl. No.: 357,912

[22] Filed: Mar. 15, 1982

[51] Int. Cl.$^3$ .................. C08G 22/10; C08G 53/08
[52] U.S. Cl. ............................. 528/65; 528/59; 2/16
[58] Field of Search ........................... 528/65, 59

[56] References Cited

U.S. PATENT DOCUMENTS

| | | | |
|---|---|---|---|
| 2,621,166 | 12/1952 | Schmidt et al. | 525/440 |
| 2,625,535 | 1/1953 | Mastin | 528/74 |
| 2,770,612 | 11/1956 | Schollenberger | 525/440 |
| 2,899,411 | 8/1959 | Schollenberger | 528/76 |
| 2,968,575 | 1/1961 | Mallonee | 106/287 |
| 2,998,403 | 8/1961 | Müller et al. | 528/76 |
| 3,382,138 | 5/1968 | Barth | 161/190 |
| 3,411,982 | 11/1968 | Kavalir et al. | 161/242 |
| 3,591,561 | 7/1971 | Kazama et al. | 528/59 |
| 3,664,979 | 5/1972 | Tanomura et al. | 528/65 |
| 3,684,770 | 8/1972 | Meisert et al. | 528/65 |
| 3,689,443 | 9/1972 | Fensch | 525/411 |
| 3,804,812 | 4/1974 | Koroscil | 528/65 |
| 3,813,695 | 6/1974 | Podell et al. | 2/168 |
| 3,846,378 | 11/1974 | Griswold | 428/365 |
| 3,872,515 | 3/1975 | Miner et al. | 2/168 |
| 3,879,764 | 4/1975 | Weber-Liel | 2/167 |
| 3,883,899 | 5/1975 | Ganz | 2/168 |
| 4,064,564 | 12/1977 | Casey | 2/168 |
| 4,131,604 | 12/1978 | Szycher | 528/79 |

OTHER PUBLICATIONS

Elastomerics, "Polyurethane Latexes for Coagulation Dipping," Sadowski, et al., Aug. 1978, pp. 17-20.
Polymers in Medicine & Surgery, Kronenthal, et al., Plenum Press, vol. 8, pp. 45 etc.

Primary Examiner—John Kight, III
Assistant Examiner—M. L. Moore
Attorney, Agent, or Firm—Biebel, French & Nauman

[57] ABSTRACT

A soft, low modulus, non-crystalline segmented polyurethane characterized by a 100% modulus less than about 250 psi, initial tensile set less than about 30% and tensile strength of about 3500 to 6500 psi obtained by balancing the percent hard segment and the degree of cross-linking within the ranges 14 to 25% hard segment and 5,000 to 30,000 molecular weight per cross-link in a segmented polyurethane; and a flexible glove for use by surgeons and others which is easily donned and comfortable on the hand, wherein the glove forming material consists essentially of the aforesaid polyurethane.

42 Claims, 1 Drawing Figure

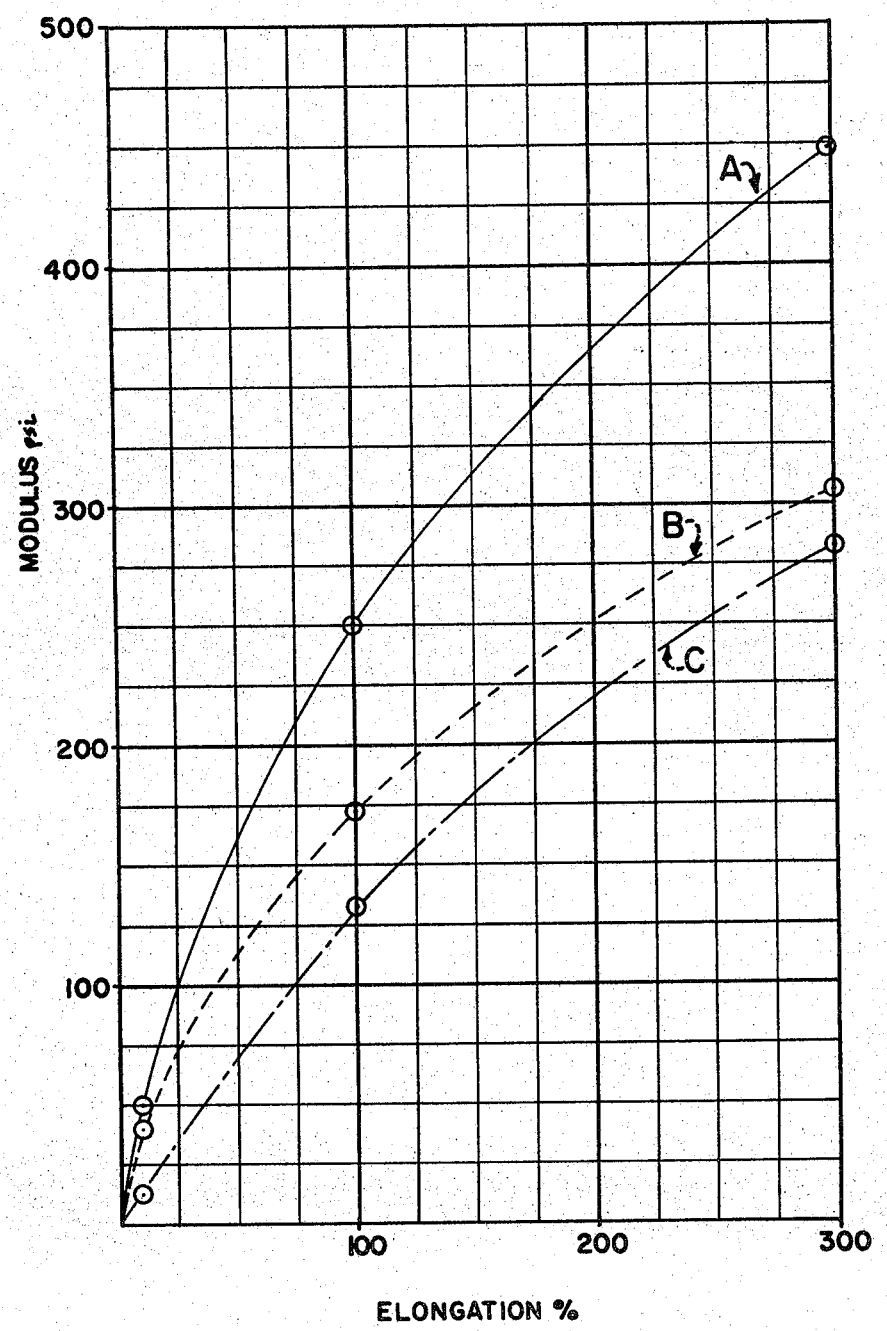

POLYURETHANE ELASTOMER AND AN IMPROVED HYPOALLERGENIC POLYURETHANE FLEXIBLE GLOVE PREPARED THEREFROM

BACKGROUND OF THE INVENTION

The present invention relates to a polyurethane elastomer and to a hypoallergenic polyurethane glove for use by surgeons and others which is easily donned, is comfortable on the hand and has good tear resistance prepared therefrom.

Usually, gloves of a flexible nature which fit the hand with a skin-tight fit (so called surgical gloves) are made from rubber compositions such as rubber cements and latexes. These compositions are hyperallergenic and 5% of those who regularly wear these gloves suffer from a type of dermatitis. The cause of the dermatitis is believed to be natural impurities which occur in the rubber latex or additives such as the curing agent, antioxidant, or the like. Attempts to remove these additives and impurities or to reduce them to nonallergenic levels have not been totally successful or economically attractive.

One approach to overcome the allergenicity problem has been to manufacture the glove of a non-allergenic or hypoallergenic biocompatable material. In this regard, Miner et al, U.S. Pat. No. 3,872,515 discloses a flexible glove made using silastic rubber.

Polyurethanes have also been used for this purpose and are very advantageous because they are biocompatible, they can be formed into films with high water vapor transmission, they are cooler to wear, and they are oil resistant and do not swell and bag on the hand in the presence of body oils. They also provide good tactility. However, it is difficult to obtain a polyurethane having good film forming properties that provides a glove that is easily donned and does not constrict the hand.

A number of drawbacks occur when polyurethanes are used in the manufacture of surgical gloves. In particular, due to the higher modulus of many polyurethanes they do not provide a glove that can be easily donned and which is comfortable on the hand. At the same time, it is difficult to modify conventional polymers to increase their softness and reduce modulus. Increasing the amount of soft segment to lower the modulus dilutes the hard segment and gives the polymers high set and creep. On the other hand, where the molecular weight of the soft segment is increased to improve softness, the soft segment often crystallizes and a drastic increase in modulus, directly contra the desired result, occurs. Likewise, where the amount of hard segment is reduced, there is less physical cross-linking and higher set.

The polyurethanes that have been used to fabricate surgical gloves have a much higher modulus than rubber and it has been necessary to use them as relatively thin films typically ranging from about 3.5 to 4.5 mils in thickness. If previous polyurethane films were used in the same thickness as the rubber films used in conventional gloves, the polyurethane gloves would be impossible to don and very uncomfortable to wear. At the same time from a manufacturing standpoint the thin films that have been used have not been completely satisfactory; film quality is not high and there is a high rate of rejection for film leaks.

Thus, there is a need for a non-allergenic polyurethane glove which is easily donned, comfortable and made from a comparatively low modulus polyurethane and, thus, there is a need for a very soft, low modulus polyurethane which has physical properties similar to those of rubber.

SUMMARY OF THE INVENTION

A principal object of the present invention is to provide a soft, flexible surgical glove from a polyurethane that is easily donned and comfortable on the hand.

Another object of the present invention is to provide a soft, low modulus, elastic polyurethane having low set.

Still another object of the present invention is to provide a non-crystalline polyurethane having the appropriate balance of hard segment and cross-linking to provide properties resembling natural rubber.

A further object of the present invention is to provide a low modulus, non-crystalline polyurethane elastomer having a relatively short cure time (e.g., about 30 min) from a long chain diol, a polyhydroxy cross-linking agent, and a polyisocyanate and which is, in the preferred case, extended using a short chain diol.

These and other objects of the present invention are attained using an essentially non-crystalline segmented polyurethane having a 100% modulus less than approximately 250 psi, initial tensile set less than approximately 30% and tensile of approximately 3500 to 6500 psi. In addition, preferred polymers have a 300% modulus of approximately 200-450 psi, elongation at break greater than 600%, and tear greater than approximately 100 ppi.

More particularly, the present invention provides a surgical glove fabricated from a segmented polyurethane having a modulus profile below the line (A) shown in the FIGURE wherein that line is defined by a 10% modulus of 50 psi, a 100% modulus of 250 psi and a 300% modulus of 450 psi.

BRIEF DESCRIPTION OF THE FIGURE

The FIGURE is drawn to scale and graphs modulus profile (stress vs. strain) for 0 to 300% elongation for the polyurethanes used in the invention gloves (lines A and B). As a reference, the figure also provides the modulus profile of a rubber used in a commercial rubber glove (line C).

DEFINITIONS

The following terms are used in describing the invention.

The term segmented polyurethanes as used herein includes both polyurethanes wherein the hard segment is formed by a single polyisocyanate monomer and polymers in which the hard segment is formed by two or more isocyanate monomers interconnected by short chain diols.

The invention polyurethanes and long chain diols are said to be amorphous or non-crystalline when they are essentially non-crystalline and they do not crystallize appreciably at room temperature.

Percent hard segment is the percent isocyanate plus any extender based on the total weight of the polymer.

Tear is Die C tear and measured in accordance with ASTM D624.

Tensile, modulus and elongation are measured in accordance ASTM D412-68.

Initial tensile set as used herein is the percent set as determined immediately after testing elongation in accordance with ASTM D412-68 by measuring the percent increase between 1 inch markings without allowing time for recovery. [Due to the tendency of the physical properties of a polyurethane to change with time, the values used herein are equilibrium values and are generally reached 3 to 4 weeks after manufacture.]

Molecular weight per cross-link ($M_c$) is calculated as set forth in POLYURETHANE CHEMISTRY AND TECHNOLOGY, Saunders and Frisch, Robert E. Krieger Publishing co., Huntington, N.Y. (1978) p. 266.

DETAILED DESCRIPTION OF THE INVENTION

The solid line A in the FIGURE, defines the maximum modulus profile for the polyurethanes used in the present invention from 0 to 300% elongation. The broken line B in the FIGURE is the modulus profile for the polyurethane illustrated in Example 14, a preferred polyurethane which yields desirable properties as a surgical glove. The broken and dotted line C is the modulus profile for a typical natural rubber. The rubber modulus profile is used herein as representative of the physical properties desirable in a polyurethane surgical glove. As can be seen from the FIGURE, the invention gloves are characterized by a low modulus polyurethane having a modulus profile below line A which approximates the elastic performance of rubber. Polyurethanes having a modulus profile above line A provide gloves which tend to constrict and tire the hand of the wearer and which are difficult to don. Thus, the present invention resides in a polyurethane surgical glove which is hypoallergenic and which is made from a polyurethane having a modulus profile approximating that of rubber. The preferred polyurethanes used in the present invention have a modulus profile on or below the line B in the FIGURE.

These properties are obtained in a segmented polyurethane derived from a long chain diol in which the amount of hard segment and the degree of cross-linking are balanced such that the polymer is essentially non-crystalline and has low modulus and low set.

Segmented polyurethanes are block copolymers constituted by alternating sequences of hard, rigid segments and soft, flexible segments. One discussion of their chemistry is found in *Polymer Science and Technology*, "Polymers in Medicine and Surgery", Kronenthal et al, Vol. 8, pp. 45–75. Generally, the hard and soft segments in these polymers are incompatible such that microphase separation or domain formation occurs. Where the soft segment is dominant, the hard segment domains serve as physical cross links and give the polymers elastomeric properties.

In the invention polymers the hard segment and degree of cross-linking are balanced within the ranges of approximately 14 to 25% hard segment and approximately 5,000 to 30,000 molecular weight per cross-link ($M_c$). Preferred polymers in accordance with the invention contain units of polyester and/or polyether diols providing a soft segment average molecular weight in the range of approximately 500 to 5000. Still more preferred polymers contain approximately 17 to 22% hard segment and 8,000 to 25,000 Mc. Generally, the invention polymer provide a Shore A of about 45 to 60 and preferably 45 to 55.

A number of problems are encountered in achieving low modulus and low set in a polyurethane elastomer. Although polymers containing greater than 25% hard segment may be non-crystalline and have low set, due to the rigidity caused by the high amount of hard segment in these polymers, they are unsatisfactory for applications where very low modulus is required. Accordingly, in the present invention the amount of hard segment is limited to a maximum of 25% by weight. However, when the hard segment is limited to 25% maximum there is insufficient domain formation or physical cross-linking for low set, e.g., some of these polymers have poor elastic memory and tend to creep and cold flow when extended. This is particularly true where the long chain diol is highly amorphous. For this reason, a degree of chemical cross-linking is relied upon in the invention polymers to fix the polymeric matrix and thereby improve set and overall elasticity. Thus, in accordance with the invention softness is obtained in an essentially non-crystalline polymer with low set by a combination of physical and chemical cross-linking.

Another problem encountered in arriving at a very low modulus polyurethane elastomer is that in many cases the long chain diol incorporated in the polymer gradually crystallizes and produces a drastic increase in the modulus. By cross-linking the polymer it is possible to lock the diol into an essentially non-crystalline conformation and obtain modulus stability in a polymer which would otherwise crystallize into a rigid, inelastic sheet. Thus, in the first instance physical and chemical cross-linking are balanced in the invention polymers to obtain elastic properties in a low modulus polymer. In the second instance, principally chemical cross-linking but in a related sense also physical cross-linking is used to reduce crystallization. This enables one to build a soft polyurethane elastomer from polyisocyanates and diols that provide the desired low modulus (as well as the desired elongation, tear and tensile in the preferred case) and, at the same time, avoid high set and crystallization due to the high molecular weight diol.

The desired properties are also obtained through selecting a long chain diol or combination of diols which tend to crystallize little at ambient temperatures in the polymer. Thus, while the present invention can be viewed as building sufficient physical and chemical cross-linking in a polyurethane so as to obtain elastomeric properties, minimize crystallization, and reduce set, by also selecting a diol or combination of diols which remains amorphous at ambient temperatures or has a low affinity for crystallization in the polymers at those temperatures, it is possible to achieve low set and minimize crystallization and, at the same time, maintain a low modulus. Where the diol component is more crystalline, the degree of cross-linking required to minimize its crystallization often produces a modulus too high for this invention.

Representative invention polymers comprise approximately 13 to 23% isocyanate, approximately 70 to 84% long chain diol and approximately 0.75 to 6% of a cross-linking agent. While a short chain diol extender is not necessarily present, when it is present it is used in an amount of approximately 0.5 to 3.0%.

It has been found that low modulus is available in these polyurethanes with good elastic and tensile properties such that a surgical glove can be obtained that is comfortable to don and wear and provides a good fit on the hand. Other polyurethanes can also be used in the present invention provided they have the requisite modulus profile as defined by curve A in the FIGURE.

In preferred polymers there is a high degree of incompatibility between the hard and soft segments such that there is a strong affinity within the hard and soft segments which leads to segmentation or domain formation. Where the polyisocyanate is aromatic or alicyclic and the long chain diol is aliphatic, this occurs quite readily. Representative polyisocyanates useful in the present invention include aromatic and alicyclic diisocyanates such as 4,4'-diphenyl methane diisocyanate (MDI), toluene diisocyanate (TDI), isophorone diisocyanate (IPDI), methylene bis (4-cyclohexyl isocyanate) (HMDI), etc. Of these MDI and HMDI, are particularly preferred. In addition to the aforementioned diisocyanates, the invention can also be practiced using aromatic and cycloaliphatic triisocyanates and tetraisocyanates.

It has been found that methylene bis (4-cyclohexyl isocyanate) (HMDI) is a particularly desirable polyisocyanate for the manufacture of a low modulus polyurethane elastomer having low set and good tear. Using HMDI as the polyisocyanate readily provides polyurethanes having 100% modulus less than 250 psi and tear significantly greater than 150 ppi. In particular, it has been found that polyurethanes having tear greater than 200 ppi are almost routinely available using HMDI and balancing hard segment and cross linking degree as discussed herein. Furthermore, unlike polyurethanes prepared from other diisocyanates, it appears that HMDI polyurethane films may be formed by solution coating processes. Whereas leaks often occur in films formed by solution coating prepolymers of other polyurethanes due to solvent bubbles, this does not seem to plague the use of HMDI derived polymers.

Various extenders can be used in the present invention. In the most typical case the extender is a short chain diol such as a straight or branched chain diol having two or six carbon atoms in the main chain, e.g., ethylene glycol, propylene glycol, 1,4 butanediol, neopentyl glycol, etc. or an alicyclic glycol having up to 10 carbon atoms, e.g., 1,4 cyclohexane diol, 1,4 dimethylol cyclohexane, etc. The short chain cyclic glycols offer the advantage of contributing to the cyclic character of the hard segment, thereby enhancing soft segment incompatibility and the likelihood of segmentation. Another type diol that can be used in the invention is represented by Esterdiol 204 (Union Carbide). Hydroquinone bis (hydroxyethyl ether) is an advantageous extender with polyether polyols as the soft segment. In the most typical case, however, the extender is 1,4 butanediol. The polymer properties tend to be superior when the extender hydroxyl groups are primary hydroxyl groups. In accordance with another embodiment of the invention, the polyurethane may be chemically cross-linked using a cross-linker which is built into the hard segment. Thus, in accordance with this embodiment, the hard segment extender is a polyol such as trimethylol propane, glycerol, etc.

In making the invention polymers, the extender, when present, is used in a molar ratio to the polyfunctional isocyanate of approximately 0.05 to 5.0 so as to provide a hard segment in the range 14 to 25% as earlier disclosed. In terms of weight percent, the extender is usually used in an amount of about 0.5 to 3.0% by weight. It is possible to control the degree of domain formation and physical cross-linking by adjusting the amount of extender.

The long chain diols useful in the present invention may be polyether diols or polyester diols and range in average molecular weight from approximately 500 to 5000 and preferably from 1000 to 3000. Some representative examples of the long chain polyester diols are polylactones such as polycaprolactone glycol, and copolymers of short chain diols and aliphatic dicarboxylic acids such as poly (ethylene adipate) glycol, poly(ethylene succinate) glycol, poly(ethylene sebacate) glycol, poly(butylene adipate) glycol, poly(ethylene butylene adipate) glycol, poly(diethylene ether adipate) etc. The polyester glycols are preferably derived from short chain diols, preferably primary diols or mixtures of primary diols having 2–4 carbon atoms and an aliphatic dicarboxylic acid having 4 to 10 carbon atoms.

In addition to the aforementioned polyesters polyols, polyether polyols can also be used in the present invention. Two polyether polyols that have been used with some success are 1000 and 2000 MW poly(tetramethylene ether) glycols. These polyols are commercially available as Polymeg 1000 (Quaker Oats, Co., Chemical Division) and Teracol 2000 (du Pont).

Many of the long chain diols are crystalline at room temperature and/or may crystallize over time in the cured glove polymer. To prevent this it is desirable to use a mixture of long chain diols to depress the crystalline melting point of the polymer. The mixture may be one of different average molecular weight glycols or a mixture of chemically different glycols such as a mixture of polycaprolactone glycol and poly(ethylene adipate) glycol or poly(ethylene butylene adipate) glycol. For example, whereas a polymer containing solely polycaprolactone glycol as the soft segment undergoes a significant increase in modulus upon storage at 5° C. for only 10 days due to crystallization, polymers containing a mixed soft segment of polycaprolactone glycols and poly(ethylene adipate) glycols provide a relatively low and stable modulus at room temperature and at 5° C., The proportions of the polyesters making up the mixed soft segment will vary depending upon the nature of the polyesters used. For illustration, in the examples below the effect of substituting polyethylene adipate glycol for polycaprolactone is illustrated. A preferred ratio of polycaprolactone glycol to poly(ethylene adipate) glycol in the invention polymers is approximately 1/3 to 3/1. Of course, some crystalline long chain diols (generally those having a crystalline melting points slightly above room temperature) do not crystallize in the polyurethane because in the polyurethane they are prevented by cross-linking from settling into a crystalline conformation or due to melting point depression which accompanies their incorporation into the polymer. Poly(ethylene adipate) glycol is one such diol and is preferred for use in the present invention.

In the invention glove polymers, the percent hard segment and the degree of cross-linking are adjusted for the diols used such that the polymer is essentially non-crystalline and has low set. It is also particularly desirable that the polyurethane films used in the present invention be essentially non-crystalline and non-crystallizable at temperatures of approximately 5° C. for at least four months. The latter requirement assures desirable storage stability and diol selection and degree of cross-linking are preferably adjusted to obtain this result.

One simple means of chemically cross-linking the invention polymers is to use a polyfunctional alcohol (i.e., compounds having three or more hydroxyl groups) in the polymer. Such compounds may be simple polyfunctional alcohols like trimethylolpropane or an adduct of a longer chain and a (short chain) polyfunctional alcohol. One that is often used is PCP-0300 (an adduct of trimethylolpropane and epsilon-caprolactone available from Union Carbide). In addition, other polyfunctional alcohols such as trimethylolethane and pentaerythritol can be used. Preferred cross-linking agents contain primary hydroxy groups.

One example of a polyurethane used in the present invention is prepared by reacting MDI and 1,4-butanediol (as the hard segment component) and a mixture of polyethylene adipate glycol (2000 MW), polycaprolactone glycol and PCP-0300.

The polyurethanes of the present invention may be prepared in a conventional manner. For example, the diols (long chain diol, cross-linking agent and extender) are mixed and heated to about 50° C. To this mixture is added a melt of the polyisocyanate and then a polymerization catalyst. Alternatively, the catalyst can be added to the diols. Any of the metal salts of organic acids which are commonly used to catalyze polyurethane polymerizations such as dibutyl tin dilaurate can be used in the invention.

In film forming processes, however, the invention polymers are prepared from prepolymers. The prepolymers used in the present invention may be prepared by stopping the polymerization reaction which produces the low modulus polyurethanes at an intermediate stage. A number of conventional techniques may be employed for this purpose but one that has been found to be particularly useful on a glove production line is to add an end-blocking agent to the polyurethane reaction mixture. A particularly useful end blocking agent is a heat-reversible end-blocking agent such as acetone oxime which can be removed to cure the prepolymer by merely heating to about 150° C. These prepolymers are formed using well known polyurethane polymerization catalysts such as dibutyl tin dilaurate. One procedure that is useful in preparing the prepolymers is disclosed in U.S. Pat. No. 3,846,378 to Griswold wherein a mixture of the diols, the cross-linking agent, and the end blocking agent is prepared and the mixture is heated. To this mixture is added the diisocyanate and the polymerization catalyst is then added. The reaction thereafter proceeds under its own reaction heat. The end-blocking agent is generally used in an amount equivalent to approximately 5 to 30% of the diisocyanate.

The invention polyurethanes are useful in many applications. In particular, films thereof can be used in manufacturing a hypoallergenic surgical glove which is easily donned and comfortable to wear. They are also useful wherever a material is required to be biocompatible and have low modulus including in prophylactics, catheter balloons, etc.

The polyurethane films used in the invention gloves may range from approximately 3.5 to 7.0 mils in thickness and readily provide a leak free, comfortable glove that is easy to don when they are used in thicknesses ranging from 4.5 to 6.5 mils.

The invention glove is prepared by coating a glove form with a film of a polyurethane prepolymer and curing it to the full elastomer. The prepolymer can be applied to the glove form by solution dip coating but is more preferably applied by a combination of dip coating and powder coating or powder coating alone. It is difficult (with the possible exception of the HMDI derived polyurethane) to obtain a glove that is pore free by solution dip coating alone because several dips are required to build up sufficient film thickness and in building up the film and removing the solvent, solvent bubbles often form which burst as the film is heated to remove the solvent and leave pores in the film.

The preferred glove forming process is to prime the glove form with a thin film (e.g., 1.0 to 3.0 mils) of polyurethane by solution dip coating followed by curing the primer film and immersing the primed form in a fluidized bed of prepolymer powder to build up the glove thickness (e.g., approximately 2 to 4 mils additional).

The solution coating compositions used in the aforementioned process are prepared by dissolving the polyurethane prepolymer in a suitable solvent. Many solvents can be used, but preferred solvents have a high solubility for the prepolymer, a low boiling point and low toxicity. One solvent that has been found particularly convenient for use in the invention is methylene dichloride. Typical solution coating compositions contain approximately 15-20% solids. These concentrations provide good film-forming viscosities.

The gloves may be formed on commercially available porcelain or metallic glove forms in the present invention. Due to the high adhesion of the polyurethane, however, the forms must be surface treated to obtain adequate release properties. One treatment that can be used is to coat the forms with a release agent such as a silicone. Another technique is to use a specially prepared form having a surface of poly(tetrafluoroethylene). Other techniques conventionally used for mold release are also effective. To further enhance release, the polyurethanes used in the invention are preferably modified to incorporate a release agent such as a long chain silicon diol like Dow Corning's Q4-3667.

Appropriately prepared glove forms are primed by dipping the form into the coating solution of polyurethane prepolymer. When using methylene dichloride and other highly volatile solvents, the glove form should be cooled to 15°-20° C. before dipping to prevent the solvent from evaporating too rapidly upon contact with the surface of the form. The thickness of the primer film is a function of the viscosity of the coating solution and the rate with which the glove form is removed from the coating solution. The faster the form is removed from the solution, the thicker the film. Preferably the primer film ranges from approximately 1 to 3 mils in thickness.

After coating the form with the primer film, the primer film is dried and cured. The film is essentially fully cured, however, a minor amount of unreacted isocyanate functionality is reserved in the primer film and used in interfacial chemical bonding with the powder coated film. The temperature and cure time of the primer film will vary with the nature of the prepolymer and the thickness of the film. As an illustration, for primer films approximately 1 to 3 mils thick using acetone oxime as the end-blocking agent, the primer film is heated at 130°-170° C. for 5 to 30 minutes.

Turning to the powder coating portion of the glove forming process, crystalline prepolymers are used in this portion of the process and are ground to a weight average particle size of approximately 1 to 100 microns and, preferably 20 to 75 microns. These powders are fluidized to produce a fluidized bed using a fluidizing gas such as air or dry nitrogen. The glove form is heated prior to being immersed in the fluidized bed such that upon contact with the glove form the powder fuses and adheres to the form. The temperature of the form will vary with the crystalline melt point of the polymer and the thickness desired in the powder coated film. Usually, the temperature of the form is at least 10° C. higher and preferably 30° to 60° C. higher than the crystalline melt point of the prepolymer so that the prepolymer fuses and adheres to the form as it contacts the form in the fluidized bed. By increasing the temperature of the form, the amount of powder picked up can be increased, and the film thickness thereby varied. Furthermore, depending on the temperature of the form, the powder may simply attach to the form in which case the powder is fused into a film later, or the powder may immediately melt out into a thin continuous film.

The glove forms may be heated differentially to impart a temperature profile to the form whereby the powder pick up can be controlled. By pre-heating certain portions of a glove form to higher temperatures, the film thickness can be increased or coating variations due to differences in immersion time and bed temperature can be compensated. For example, it is desirable to make the cuff thicker than the balance of the glove since the cuff is used to pull the glove onto the hand. Differential heating is also useful to compensate for differences in immersion time when dipping a form into and out of a bed where the first portions to enter the bed are also the last to leave and therefor have the opportunity accumulate more polymer. As an illustration, when making surgical gloves by dipping the fingers first, the fingers are pre-heated to a lower temperature since they are the first to enter and the last to leave the powder bed.

Generally powder coating is relied upon in the process to enhance the film thickness by approximately 2 to 4 mils. This provides a glove product which is approximately 3.5 to 6.0 mils thick. It has been found that polyurethane prepolymer particles coated onto a primer film as in the present invention, with heating, uniformly flow out on the primer film and form a thin continuous film.

Following powder coating, the glove form is heated and the powder coated film and the unreacted isocyanate in the primer film are cured together. As in the case of curing the primer film, the heating conditions used to fully cure the powder coated film varies with the nature of the prepolymers and the thickness of the film. Using the prepolymer described in the example below, the glove product is obtained by heating the powder coated and primed form approximately 10 to 30 minutes at 150° to 180° C. It will be appreciated that the short cure times required by acetone oxime end-blocked polyurethanes make the process suitable for commercial production lines.

Generally, gloves formed in the invention are pigmented. The pigment can be fluidized with the polyurethane prepolymer particles and co-deposited on the primer film therewith. As a rule, conventional pigments such as umber and $TiO_2$ can be used in the invention process in their commercially available fine particle size.

It should be apparent that to use the combined solution dip-powder coating procedures, the polyurethane prepolymer must be crystalline so as to be grindable as the prepolymer, but non-crystalline as the cured glove film. One technique that can be used to expand the range of useful prepolymers for use in this process is to grind the prepolymer while it is cooled to crystallize it and to cool the fluidized powder bed. Generally, useful prepolymers for making the invention glove via powder coating have crystalline melting points from about 10° C. to 45° C. Such prepolymers are available by reacting an organic diisocyanate with a long chain diol such as polycaprolactone glycol and poly(ethylene adipate) glycol.

As a further improvement, the present invention also provides a so called powderless glove. Powderless gloves are readily available when powder coating techniques are used to form the invention gloves as described above. In particular, a solid lubricant such as silica, a finely divided epoxy, a hard polyurethane or nylon particle (e.g., about 5 to 80 microns) can be admixed in the fluidized bed and powder coated on the glove form with the polyurethane prepolymer. When the polyurethane particles are melted out and cured, the solid lubricant becomes embedded in the glove and provides a slight surface protrusion on the face of the glove which becomes the inside surface worn adjacent the skin. These protrusions enable the wearer to slip his hand into the glove without an auxiliary lubricant such as starch that is conventionally used to facilitate donning of surgical gloves. Another technique that can be used to form a powderless glove is to spray the surface of the glove with a solid lubricant when the polyurethane is in a tacky, unfully cured stage such that it is embedded in the glove surface as the polymer cures.

The invention is illustrated in more detail by the following non-limiting examples. Unless otherwise indicated, all parts are by weight.

EXAMPLE 1

A polyurethane elastomer was prepared by mixing 10 grams of a 540 MW polycaprolactone triol (Union Carbide PCP-0300), 117 g of a 1250 MW polcaprolactone diol (Union Carbide PCP-0230), 153 g of a 2,000 MW polycaprolactone diol (Union Carbide PCP-0240), 23 g of Dow Corning Q4-3667 (a long chain silicon diol) and 9 g of 1,4 butanediol in a suitable reactor and heating the mixture to 50° C. To this mixture was added 82 g of molten 4,4' diphenyl methane diisocyanate and 0.12 g of dibutyl tin dilaurate (M+T chemical, T-12). A solid polyurethane was obtained having the properties set forth in Table I below. Unless otherwise indicated, all percents are by weight.

TABLE I

| | |
|---|---|
| Hard Segment % | 22.7 |
| $M_c$ | 16,600 |
| Long Chain Diol % | 73 |
| Cross-linking agent % | 2.5 |
| Isocyanate % | 20.8 |
| Tensile (psi) | 5,500 |
| Modulus | |
| Youngs (psi) | 390 |
| 100% (psi) | 140 |
| 300% (psi) | — |
| Elongation % | 605 |
| Tear (ppi) | 115 |
| Set % | 13 |

EXAMPLE 2

Using the same procedure as Example I, a polyurethane prepolymer was prepared by mixing 8 g 540 MW polycaprolactone triol (PCP-0300), 319 g 2000 MW poly(ethYlene-butylene) adipate glycol 7 g 1,4 butanediol and 5 g acetone oxime, and adding to the heated mixture 66 g 4,4' diphenyl methane diisocyanate with 0.12 g dibutyl tin dilaurate. The polyurethane obtained upon heating the prepolymer had the properties shown in Table II.

TABLE II

| | |
|---|---|
| Hard Segment (%) | 18 |
| $M_c$ | 19,400 |

TABLE II-continued

| | |
|---|---|
| Long Chain diol (%) | 79.7 |
| Crosslinking agent (%) | 2.1 |
| Isocyanate content, (%) | 16.6 |
| Tensile psi | 3500 |
| Modulus | |
| Youngs, psi | 310 |
| 100%, psi | 190 |
| 300%, psi | 280 |
| Elongation (%) | 760 |
| Tear (ppi) | 110 |
| Set (%) | 11 |

EXAMPLES 3 and 4

Polyurethanes were prepared from the reactants set forth in Table III below by the procedure set forth in Example 1. The polyurethanes obtained had the compositions and physical properties as shown in Table III.

TABLE III

| | Ex. 3 | Ex. 4 |
|---|---|---|
| 540 M.W. Polycaprolactone Triol (PCP 0300) | 9 g | 13 g |
| 2000 M.W. Poly(ethylene adipate) glycol | 279 g | 237 g |
| 1000 M.W. Poly(ethylene adipate) glycol | 0 g | 30 g |
| Dow Corning Q4-3667 | 24 g | 28 g |
| 1,4 Butanediol | 10 g | 9 g |
| 4,4' diphenyl methane diisocyanate | 73 g | 77 g |
| Dibutyl Tin Dilaurate | 0.12 g | 0.12 g |
| Hard Segment (%) | 20.7 | 21.5 |
| $M_c$ | 17,300 | 13,200 |
| Long chain diol (%) | 75.6 | 73.8 |
| Crosslinking agent, (%) | 2.3 | 3.2 |
| Isocyanate content, (%) | 18 | 19 |
| 2 Month Physicals | | |
| Tensile (psi) | 6600 | 3800 |
| Modulus | | |
| Youngs (psi) | 420 | 320 |
| 100% (psi) | 170 | 130 |
| 300% (psi) | 350 | 240 |
| 500% (psi) | 1300 | 650 |
| Elongation (%) | 750 | 690 |
| Tear (ppi) | 140 | 105 |
| Set (0/6) | 11 | 10 |

EXAMPLES 5-8

To demonstrate the effect of the degree of cross-linking on the physical properties of the invention polymers, five polymer samples were prepared in accordance with Table IV below using the procedure in Example 1. The Control example is a polyurethane having a low level of chemical cross-linking (i.e., a high $M_c$ value). Examples 5-8 are polyurethanes in accordance with the present invention in which the control example has been modified by increasing amounts of cross-linking agent (PCP-0300). The properties obtained are shown in Table IV below.

TABLE IV

| | Control | Ex. 5 | Ex. 6 | Ex. 7 | Ex. 8 |
|---|---|---|---|---|---|
| 540 MW Polycaprolactone triol (PCP0300) | 3 g | 6 g | 10 g | 13 g | 17 g |
| 1250 MW Polycaprolactone diol (PCP0230) | 139 g | 130 g | 122 g | 113 g | 103 g |
| 2000 MW Polycaprolactone diol (PCP0240) | 108 g | 110 g | 113 g | 115 g | 117 g |
| Dow Corning Q4-3667 | 59 g | 61 g | 62 g | 63 g | 65 g |
| 1,4 Butane diol | 8 g | 8 g | 9 g | 9 g | 9 g |
| 4,4' diphenyl methane diisocyanate | 76 g | 78 g | 79 g | 81 g | 83 g |
| Dibutyl Tin Dilaurate | 0.12 g | 0.12 g | 0.12 g | 0.12% | 0.12% |
| Hard Segment, (%) | 21.1 | 21.5 | 21.9 | 22.4 | 22.9 |
| $M_c$ | 33,300 | 21,800 | 16,000 | 12,500 | 10,200 |
| Long chain diol, (&) | 76.6 | 75.4 | 74.1 | 72.7 | 71.2 |
| Crosslinking agent (%) | 0.8 | 1.6 | 2.4 | 3.3 | 4.2 |
| Isocyanate content (%) | 19.0 | 19 | 20 | 20 | 21 |
| 2 Month Physicals | | | | | |
| Tensile, psi | 3900 | 4200 | 4700 | 4000 | 5000 |
| Modulus | | | | | |
| Youngs, psi | 390 | 350 | 350 | 340 | 370 |
| 100%, psi | 150 | 150 | 170 | 180 | 190 |
| 300%, psi | 240 | 250 | 320 | 340 | 380 |
| Elongation, % | 730 | 680 | 630 | 630 | 580 |
| Tear, ppi | 140 | 130 | 140 | 130 | 110 |
| Set, % | 40 | 20 | 11 | 10 | 9 |

The results in Table IV demonstrate that as the degree of cross-linking increases (lower $M_c$) within the claimed limits, set is improved without reducing modulus. A comparison of the control sample with Example 5-8 also shows that where $M_c$ is outside the claimed range the polymer has high set.

EXAMPLE 9

A polyether polyurethane having the composition shown in Table 5 below was prepared in accordance with Example 1. The polyurethane obtained possessed a tensile strength of 4100 psi, a Youngs modulus of 470 psi, a 100% modulus of 230 psi, 600 percent elongation, 140 ppi tear, and 8% initial set.

TABLE V

| | Ex. 9 |
|---|---|
| 540 MW Polycaprolactone triol (PCP-0300 Union Carbide) | 8 g |
| 2000 MW Poly(tetramethylene ether) glycol | 31 g |
| 1,4 Butane diol | 7 g |
| 4,4' diphenyl methane diisocyanate | 69 g |
| Dibutyl Tin Dilaurate | 0.12 g |
| Hard Segment, (%) | 19.0 g |
| $M_c$ | 18,600 |
| Long Chain diol, (%) | 77.6% |
| Crosslinking Agent, (%) | 2.1% |
| Isocyanate Content, (%) | 17.1 |

EXAMPLE 10

A prepolymer was prepared by mixing 11.9 grams of a 540 MW polycaprolactone triol (Union Carbide, PCP-0300), 301.9 grams of a 3000 MW poly(ethylene-1,4-butane adipate) diol (Hooker Chemical, Rucoflex S1037-35), 15.3 grams of Dow Corning Q4-3667, 7.4 grams of 1,4-butanediol and 4.5 grams of acetone oxime in a suitable reactor and heating the mixture to 70° C. To this mixture was added with stirring 59.0 grams of methylene bis (4-cyclohexyl isocyanate) and 0.12 grams of dibutyl tin dilaurate. An elastomeric amorphous prepolymer was obtained which readily fused into a continuous film at 90°–100° C. and cured to full properties in 30 minutes at 150° C. in a suitable convection oven. A solid polyurethane was obtained having the properties listed in Table I below. Unless otherwise indicated, all percents are by weight.

TABLE 1

| Hard Segment (%) | 16.8 |
|---|---|
| Mc | 11,438 |
| Long Chain Diol (%) | 80.2 |
| Cross-linking agent (%) | 3.0 |
| Isocyanate (%) | 14.9 |
| Acetone Oxime (eq. %)* | 13.4 |
| Tensile (psi) | 4318 |
| Modulus | |
| Young's (psi) | 319 |
| 100% (psi) | 166 |
| 300% (psi) | 370 |
| Elongation % | 947 |
| Tear (ppi) | 249 |
| Set % | 8 |

*equivalent percent based on isocyanate

EXAMPLE 11

Using the same procedure set forth in Example 10, a polyurethane elastomer was prepared by mixing 11.3 grams of a 540 MW polycaprolactone triol, 128.5 grams of a 3000 MW poly(ethylene, 1,4-butane adipate) diol, 158.9 grams of a 2000 MW poly(ethylene adipate) diol, (Witco Chemical, Formrez 22-56), 17.96 grams Dow Corning Q4-3667, 8.7 grams of 1,4-butanediol and 5.2 grams of acetone oxime and adding to the heated mixture 69.5 grams of HMDI and 0.12 grams dibutyl tin dilaurate to prepare a prepolymer. The prepolymer obtained was granular and crystalline and was fused into a continuous film and cured as in Example 1. The polyurethane obtained had the properties shown in Table II.

TABLE II

| Hard Segment (%) | 19.8 |
|---|---|
| Mc | 11,106 |
| Long Chain Diol (%) | 77.3 |
| Cross-Linking Agent (%) | 2.9 |
| Isocyanate (%) | 17.6 |
| Acetone oxime (eq. %) | 13.4 |
| Tensile (psi) | 5236 |
| Modulus | |
| Young's (psi) | 384 |
| 100% (psi) | 207 |
| 300% (psi) | 482 |
| Elongation (%) | 843 |
| Tear ppi | 284 |
| Set % | 12 |

EXAMPLE 12

Using the same procedure set forth in Example 10, a prepolymer was prepared by mixing 14.6 gram of a 540 MW polycaprolactone triol, 278.58 grams of a 2000 MW poly(ethylene -1,4-butane adipate) diol, 19.1 grams of Dow Corning Q4-3667, 8.2 grams of 1,4-butane diol and 5.6 grams acetone oxime and adding to the heated mixture 73.9 grams of methylene bis (4-cyclohexyl isocyanate) and 0.12 grams of dibutyl tin dilaurate. An amorphous prepolymer was obtained which was formed into a film and cured as in Example 1. The polyurethane obtained had the properties shown in Table III.

TABLE III

| Hard Segment (%) | 20.8 |
|---|---|
| Mc | 9,134 |
| Long Chain Diol (%) | 75.5 |
| Cross-linking Agent (%) | 3.7 |
| Isocyanate (%) | 18.7 |
| Acetone Oxime (eq. %) | 13.4 |
| Tensile (psi) | 3607 |
| Modulus | |
| Young's (psi) | 366 |
| 100% (psi) | 195 |
| 300% (psi) | 453 |
| Elongation (%) | 753 |
| Tear, (ppi) | 220 |
| Set, (%) | 11 |

EXAMPLE 13

Using the same procedure set forth in Example 10, a prepolymer was prepared by mixing 12.8 grams of a 540 MW polycaprolactone triol, 230.23 grams of a 2000 MW poly(ethylene adipate) diol, 39.3 grams of a 1000 MW poly(ethylene adipate) diol (Hooker Chemical, Rucoflex S101-110), 21.05 Dow Corning Q4-3667, 9.1 grams of 1,4-butanediol and 6.2 g acetone oxime, and adding to the heated mixture 81.4 grams of methylene bis (4-cycholexyl isocyanate) and 0.12 grams of dibutyl tin dilaurate. A crystalline, grindable prepolymer was obtained which fused into a film and was cured as in Example 10. The polyurethane obtained had the properties shown in Table IV.

TABLE IV

| Hard Segment % | 23.0 |
|---|---|
| Mc | 9,476 |
| Long Chain Diol (%) | 73.8 |
| Crosslinking Agent (%) | 3.2 |
| Isocyanate (%) | 20.7 |
| Acetone Oxime (eq %) | 13.4 |
| Tensile (psi) | 4782 |
| Modulus | |
| Young's (ppi) | 412 |
| 100% (psi) | 207 |
| 300% (psi) | 497 |
| Elongation (%) | 755 |
| Tear (ppi) | 210 |
| Set, (%) | 23 |

EXAMPLE 14

A polyurethane prepolymer was obtained by preparing a diol mixture containing 22 parts of a 540 MW polycaprolactone triol (Union Carbide PCP-0300), 703 parts of 2000 MW poly(ethylene adipate) glycol (Formrez 24-56, Witco Chemical Co.), 24 parts of 1,4 butanediol, and 58 parts of Dow Corning Q4-3667 silicone diol, as a release assistant, 14 parts of acetone oxime and 0.3 parts of dibutyl tin dilaurate. The diol mixture was heated to 50° C. and 179 parts of 4,4' diphenyl methane diisocyanate were added thereto at a mixing head which heated to 90° C. under the reaction exotherm. The reaction product was poured into a pan to form a solid slab and allowed to stand 3 days at room temperature.

Prepolymer prepared as above was divided into two portions. One portion was dissolved in methylene dichloride to produce a solution for dip coating and the other portion was ground to an average particle size of about 50 microns and fluidized with dry nitrogen.

A glove form suitably prepared was cooled to 15° C. and dipped into a 20% solids solution of the prepolymer obtained as above to obtain a film 1.5 mils thick. This film was cured at 150° C. for about 10 min. The primed form was thereafter heated to about 120° C. and immersed in the fluidized bed of the prepolymer particle obtained as above to build up a film 4.5 to 6.0 mils total thickness. This film was cured at 160° C. for 15 min whereafter it was removed from the form to provide a glove having the following properties.

| | |
|---|---|
| Tensile (psi) | 5900 |
| 10% Mod. (psi) | 43 |
| 100% Mod. (psi) | 171 |
| 300% Mod. (psi) | 307 |
| Elongation (%) | 787 |
| Tear (ppi) | 148 |
| Set (%) | 21-8 |
| Oil Immersion | |
| 2 hrs.-100° F.-ASTM | |
| #5 Oil | |
| Swell (%) | 0 |
| Tear (ppi) | 125 |
| Tensile (psi) | 5500 |
| Elongation (%) | 750 |
| Water Vapor Transmission | |
| (a) gm/mil/100 in$^2$/24 hrs/108° F. | 320 |
| (b) gm/100 in$^2$ 24 hrs/108° F. | 55 |

Having described the invention in detail and by reference to specific embodiments thereof, it will be apparent that numerous variations and modification are possible without departing from the spirit and scope of the following claims.

What is claimed is:

1. A flexible glove made from a polyurethane having 100% modulus less than approximately 250 psi, a 300% modulus of 200 to 450 psi, initial tensile set less than approximately 30% and tesile strength of approximately 3500 to 6500 psi.

2. The flexible glove of claim 1 wherein said polyurethane has a modulus profile below the curve (A) in the FIGURE.

3. The flexible glove of claim 2 wherein said polyurethane has tear greater than approximately 100 ppi, and greater than approximately 600% elongation.

4. The flexible glove of claim 2 wherein said polyurethane is a segmented polyurethane in which the percent hard segment is in the range of approximately 14–25% and the degree of cross-linking is approximately 5000 to 30,000 $M_c$.

5. The flexible glove of claim 4 wherein said polyurethane is the reaction product of an aromatic or alicyclic diisocyanate, a short chain diol extender, a 500–5000 molecular weight long chain diol, and a polyhydroxy cross-linking agent.

6. The flexible glove of claim 5 wherein said polyurethane is essentially non-crystalline and non-crystallizable at a temperature of 5° C. for at least four months.

7. The flexible glove of claim 6 wherein said glove has an outside surface and an inside surface, said inside surface being worn against the skin, wherein said inside surface has embedded therein a solid lubricant.

8. The flexible glove of claim 5 wherein said long chain diol comprises a polyester diol.

9. The flexible glove of claim 8 wherein said polyester diol is a poly(ethylene adipate) diol.

10. A polyurethane elastomer having 100% modulus less than approximately 250 psi, a 300% modulus of 200 to 450 psi, tensile of approximately 3500 to 6500 psi, and less than approximately 30% initial tensile set, wherein said polyurethane comprises approximately 14 to 25% hard segment, is chemically cross-linked to provide approximately 5,000 to 30,000 $M_c$, and is derived from an aromatic or alicyclic polyisocyanate and an approximately 500 to 5000 average molecular weight long chain diol that is crosslinked with a polyhydroxy crosslinking agent.

11. The polyurethane of claim 10 wherein said polyurethane provides a shore A hardness of about 40 to 60.

12. The polyurethane of claim 10 wherein said polyurethane contains about 13 to 23% polyisocyanate.

13. The polyurethane of claim 12 wherein said polyurethane contains about 0.5 to 3.0% of a short chain diol extender.

14. The polyurethane of claim 13 wherein said short chain diol is a straight chain diol containing up to six carbon atoms.

15. The polyurethane of claim 10 wherein said polyisocyanate is selected from the group consisting of 4,4'-diphenyl methane diisocyanate, toluene diisocyanate and isophorone diisocyanate.

16. The polyurethane of claim 10 wherein said polyisocyanate is methylene bis (4-cyclohexyl isocyanate).

17. The polyurethane of claim 10 wherein said long chain diol comprises a polyester diol.

18. The polyurethane of claim 17 wherein said long chain diol comprises a blend of polyester diols.

19. The polyurethane of claim 17 wherein said long chain diol is polycaprolactone glycol, poly(ethylene adipate) glycol or a blend thereof.

20. The polyurethane of claim 10 wherein said polyurethane is essentially non-crystalline at temperatures of approximately 5° C.

21. The polyurethane of claim 1 wherein said polyurethane possesses tensile of about 3500 to 6500 psi, 300% modulus of about 200 to 450 psi, elongation at break greater than about 600% and tear greater than about 100 ppi.

22. The polyurethane of claim 10 wherein said polyurethane is characterized by a modulus profile below the curve A in the FIGURE.

23. A film of the polyurethane of claim 10.

24. A film of the polyurethane of claim 16.

25. The flexible glove of claim 5 wherein said diisocyanate is selected from the group consisting of 4,4'-diphenyl methane diisocyanate, toluene diisocyanate, isophorone diisocyanate and methylene bis (4-cyclohexyl isocyanate).

26. The flexible glove of claim 5 wherein said long chain diol is a crystalline diol.

27. The flexible glove of claim 5 wherein said long chain diol is a non-crystalline diol.

28. The flexible glove of claim 5 wherein said long chain diol is selected from the group consisting of poly(ethylene adipate) glycol, poly(ethylene succinate) glycol, poly(ethylene sebacate) glycol, poly(butylene adipate) glycol, poly(ethylene adipate) glycol, poly(- diethylene ether adipate) glycol, poly(tetramethylene ether) glycol and mixtures thereof.

29. The flexible glove of claim 5 wherein said long chain diol additionally comprises a silicone diol as a mold release agent.

30. The flexible glove of claim 5 wherein said extender is a short chain diol having 2 to 6 carbon atoms in the main chain selected from the group consisting of ethylene glycol, propylene glycol, 1,4-butane diol, and neopentyl glycol, 31. The flexible glove of claim 1 wherein said polyurethane contains approximately 17 to 22% hard segment.

32. The flexible glove of claim 1 wherein said polyurethane has a modulus profile below the curve (B) in the FIGURE.

33. The flexible glove of claim 1 wherein said polyurethane is the reaction product of:
an aromatic or alicyclic diisocyanate selected from the group consisting of 4,4'-diphenyl methane diisocyanate, toluene diisocyanate, isophorone diisocyanate and methylene bis (4-cyclohexyl isocyanate),
a long chain diol having a molecular weight of approximately 500 to 5000 selected from the group consisting of poly(ethylene adipate) glycol, poly(ethylene succinate) glycol, poly(ethylene sebacate) glycol, poly(butylene adipate) glycol, poly(ethylene-butylene adipate) glycol, poly(diethylene ether adipate) glycol, and mixtures thereof,
a short chain diol extender having 2 to 6 carbon atoms selected from the group consisting of ethylene glycol, propylene glycol, 1,4-butane diol, and neopentyl glycol,
and a polyhydroxy cross-linking agent, wherein said polyurethane contains approximately 17 to 22% hard segment and has a degree of cross-linking of approximately 5000 to 30,000 $M_c$.

34. The polyurethane elastomer of claim 10 wherein said long chain diol is selected from the group consisting of poly(ehtylene adipate) glycol, poly(ethylene succinate) glycol, poly(ethylene sebacate) glycol, poly(butylene adipate) glycol, poly(ethylene-butylene adipate) glycol, poly(diethylene ether adipate) glycol, poly(tetramethylene ether) glycol and mixtures thereof.

35. The polyurethane elastomer of claim 10 wherein said long chain diol additionally comprises a silicone diol as a mold release agent.

36. The polyurethane elastomer of claim 10 wherein said polyurethane is the product of reacting:
an aromatic or alicyclic diisocyanate selected from the group consisting of 4,4'-diphenyl methane diisocyanate, toluene diisocyanate, isophorone diisocyanate and methylene bis (4-cyclohexyl isocyanate),
a long chain diol having a molecular weight of approximately 500 to 5000 selected from the group consisting of poly(ethylene adipate) glycol, poly(ethylene succinate) glycol, poly(ethylene sebacate) glycol, poly(butylene adipate) glycol, poly(ethylene-butylene adipate) glycol, poly(diethylene ether adipate) glycol, and mixtures thereof,
a short chain diol extender having 2 to 6 carbon atoms selected from the group consisting of ethylene glycol, propylene glycol, 1,4-butane diol, and neopentyl glycol,
and a polyhydroxy cross-linking agent, wherein said polyurethane contains approximately 17 to 22% hard segment and has a degree of cross-linking of approximately 5000 to 30,000 $M_c$.

37. A flexible glove formed from a polyurethane which is the reaction product of:
an aromatic or alicyclic diisocyanate selected from the group consisting of 4,4'-diphenyl methane diisocyanate, toluene diisocyanate, isophorone diisocyanate and methylene bis (4-cyclohexyl isocyanate),
a long chain diol having a molecular weight of approximately 500 to 5000 selected from the group consisting of poly(ethylene adipate) glycol, poly(ethylene succinate) glycol, poly(ethylene sebacate) glycol, poly(butylene adipate) glycol, poly(ethylene-butylene adipate) glycol, poly(diethylene ether adipate) glycol, and mixtures thereof,
a short chain diol extender having 2 to 6 carbon atoms selected from the group consisting of ethylene glycol, propylene glycol, 1,4-butane diol, and neopentyl glycol,
and a polyhydroxy crosslinking agent, wherein said diisocyanate and said extender are present in a combined amount which provides approximately 17 to 22% hard segment and said crosslinking is present in an amount which provides a degree of crosslinking of approximately 5000 to 30,000 $M_c$ wherein said polyurethane provides a 100l% modulus less than approximately 250 psi, a 300% modulus of 200 to 450 psi, initial tensile set less than approximately 30%, and tensile strength of approximately 3500 to 6500 psi.

38. The flexible glove of claim 37 wherein said long chain diol additionally comprises a silicone diol as a mold release agent.

39. The flexible glove of claim 38 wherein said polyurethane is essentially non-crystalline and non-crystallizable at temperatures of 5° C. for at least 4 months.

40. A polyurethane elastomer which is the product of:
an aromatic or alicyclic diisocyanate selected from the group consisting of 4,4'-diphenyl methane diisocyanate, toluene diisocyanate, isophorone diisocyanate and methylene bis (4-cyclohexyl isocyanate),
a long chain diol having a molecular weight of approximately 500 to 5000 selected from the group consisting of poly(ethylene adipate) glycol, poly(ethylene succinate) glycol, poly(ethylene sebacate) glycol, poly(butylene adipate) glycol, poly(ethylene-butylene adipate) glycol, poly(diethylene ether adipate) glycol,
a short chain diol extender having 2 to 6 carbon atoms selected from the group consisting of ethylene glycol, propylene glycol, 1,4-butane diol, and neopentyl glycol,
and a polyhydroxy cross-linking agent, wherein said diisocyanate and said extender are present in a combined amount which provides approximately 17 to 22% hard segment and said crosslinking agent is present in an amount which provides a degree of crosslinking of approximately 5000 to 30,000 $M_c$ wherein said polyurethane provides a 500% modulus less than approximately 250 psi, a 300% modulus of 200 to 450 psi, a tensile of approximately 3500 to 6500 psi, and less than approximately 30% initial tensile set.

41. The polyurethane elastomer of claim 40 wherein said long chain diol comprises a silicone diol as a mold release agent.

42. The polyurethane of claim 41 wherein said polyurethane is crystalline and non-crystallizable at temperatures of 5° C. for at least 4 months.

* * * * *

UNITED STATES PATENT AND TRADEMARK OFFICE
CERTIFICATE OF CORRECTION

PATENT NO. : 4,463,156
DATED : July 31, 1984
INVENTOR(S) : Charles W. McGary, Jr., et al It is certified that error appears in the above—identified patent and that said Letters Patent is hereby corrected as shown below:

Col. 15, claim 1, line 1, after "having" insert --a--.

Col. 16, claim 28, line 68, after "ethylene" insert -- -butylene--.

Col. 18, claim 37, line 24, "1001%" should be --100%--.

Signed and Sealed this

Twenty-fifth Day of December 1984

[SEAL]

Attest:

GERALD J. MOSSINGHOFF

*Attesting Officer*  *Commissioner of Patents and Trademarks*